United States Patent
Davydov et al.

[11] Patent Number: 5,281,226
[45] Date of Patent: Jan. 25, 1994

[54] MISSING PORTION OF A TUBULAR BONE

[76] Inventors: Anatoly B. Davydov, ulitsa Krasny Kazanets, 19, korpus 1, kv. 283; Sergei I. Belykh, 2-oi Krestovsky pereulok, 4, kv. 66.; July G. Shaposhnikov, ulitsa Tsakovskogo, 26, korpus 2, kv. 159.; Stanislav G. Mastlennikov, ulitsa Marshala Malinovskogo, 6, kv. 63; Oleg A. Malakhov, Orekhovy bulvar, 11, korpus 1, kv. 81, all of Moscow, U.S.S.R.

[21] Appl. No.: 646,636
[22] PCT Filed: Mar. 7, 1990
[86] PCT No.: PCT/SU90/00065
§ 371 Date: Jan. 31, 1991
§ 102(e) Date: Jan. 31, 1991
[87] PCT Pub. No.: WO90/11726
PCT Pub. Date: Oct. 18, 1990
[51] Int. Cl.⁵ .................................................. A61F 2/28
[52] U.S. Cl. ..................................... 606/62; 606/63; 606/77; 623/16
[58] Field of Search ............... 606/62, 60, 67, 73, 606/72, 63, 68, 76, 77; 623/18, 13, 20, 16

[56] References Cited

U.S. PATENT DOCUMENTS

| | | | |
|---|---|---|---|
| 3,710,789 | 1/1973 | Ersek | 606/60 |
| 3,979,779 | 9/1976 | Zeibig | 606/60 |
| 4,016,874 | 4/1977 | Maffei | 606/62 |
| 4,682,590 | 7/1987 | Kothmann | 606/62 |
| 4,938,768 | 7/1990 | Wu | 606/60 |
| 5,112,354 | 5/1992 | Sires | 623/16 |
| 5,133,755 | 7/1992 | Brekke | 623/16 |

FOREIGN PATENT DOCUMENTS

| | | | |
|---|---|---|---|
| 385580 | 6/1973 | U.S.S.R. | 606/62 |
| 2175507 | 12/1986 | United Kingdom | 623/16 |

OTHER PUBLICATIONS

I. A. Moshkovich, Operative Orthopedics, 1983, Meditsina Pub. Moscow, pp. 224–225.
"Biomekhanika", 1975, Riga, V. K. Kalnberz, et al. Clinico-biomechanical requirements, etc. pp. 365–366.

Primary Examiner—Robert A. Hafer
Assistant Examiner—David J. Kenealy
Attorney, Agent, or Firm—Keck, Mahin & Cate

[57] ABSTRACT

The device relates to reconstructive surgery and orthopedics, and includes a central rod introducible into medullary canals of bone fragments of a bone, and a tubular element fittable on the rod at the place of the missing portion of the bone, the tubular element being equidimensional with the missing portion of the bone. The tubular element is shaped as a shell made of biocompatible polymers, and a layer of a porous polymer material is insertable between the rod and the shell incorporating a biomass of homogenized bone tissues. The invention is used for restoration of missing portions of bone which have been lost due to extensive injuries or wounds or as a result of pathologic changes of the bone tissue (such as may be caused by tumors or tuberculous infections).

4 Claims, 2 Drawing Sheets

MISSING PORTION OF A TUBULAR BONE

FIELD OF THE INVENTION

The invention relates generally to reconstructive surgery and orthopedics and more specifically to a device for restoration of a missing portion of tubular bone.

BACKGROUND OF THE INVENTION

Problems of bone tissue restoration include avoiding free space between bone fragments, avoiding filling the space previously occupied by lost bone with connective tissue, and controlled evacuation of the space to leave room for the newly growing tissue.

Solution of the problem lies in the development of biocompatible polymers biodegradable under the action of body fluids within preset periods of time and technological processes for making diversely shaped finished products from such polymers, as well as technology for imparting therapeutic properties to such polymer products.

Known structures made of biologically inert materials are aimed at permanent replacement of a missing portion of bone and thus render it completely impossible to form fresh bone tissue of the patient's own making at the place involved.

A prior-art device for external immobilization of bone fragments (cf. I. A. Moshkovich, *Operative Orthopedics*, 1983, Meditsina Publishers, Moscow, pp. 224-225 (in Russian)) has a number of rings inter connected through rods and provided with intramedullary pins. Application of this device enables one to elongate a human limb by daily repeated gradual extension of the bone fragments by gradually increasing the distance between the rings. An extension cycle lasts from 20 to 80 days.

Such a device, however, is suitable for stretching sound limbs only. Besides, its application involves much work by medical staff for a prolonged period of time. Also, there is a source of permanent danger of infection at the place of introduction of the transverse pins, which may also cause contraction of ligaments. The device cannot be used where there are extensive total bone defects due to a complicated injury or gunshot wounds.

A state-of-the-art device for restoration of a missing portion of a tubular bone (cf. *Biomekhanika*, 1975, Riga, V. K. Kalnberz, et al. Clinico-biomechanical requirements imposed on the endoprosthesis of the femoral diaphysis, pp. 365-366 (in Russian)) is known to comprise a central metallic rod and a tubular element based on biologically inert composite materials, such as polymers or inorganic substances, the tubular element being fitted on the rod. The configuration and dimensions of the tubular element correspond to the missing portion of bone. During surgery, the rod is introduced into the medullary canals of the tubular bone fragments, then the tubular element is installed on the rod at the place of the missing portion of bone and fixed to the bone fragments. However, such a tubular element is very difficult to make according to the individual dimensions of patient's injury. It is extremely difficult to combine an artificial bone with the bone matrix; the bone tissue is liable to resorb at the place of contact with the artificial bone and the reaction to a large foreign body manifests itself continuously after implantation of the artificial bone. The possibility of replacement by genuine bone of the patient is ruled out completely.

SUMMARY OF THE INVENTION

It is an object of the present invention to provide a device for restoration of a missing portion of a tubular bone of a patient's limb which would ensure restoration of the function of the limb.

The object is accomplished by providing a device for restoration of a missing portion of tubular bone, comprising a central rod insertable into the medullary canals of the bone fragments, and a tubular element made of a synthetic material and fitted on the rod at the place occupied by the lost bone portion, the tubular element being equidimensional with the lost bone portion. The tubular element is shaped as a shell of polymer biocompatible with the bone tissue, and a layer of a polymeric porous material introducible between the rod and the shell and incorporating a biomass of homogenized bone tissue.

The proposed device provides for regeneration of the bone tissue of large areas of the missing bone. This is achieved by appropriate construction of the tubular element. Provision of the shell prevents the regeneration zone from being filled with soft tissue and makes it possible to retain the porous material with the biomass within the volume of the missing portion of bone in the regeneration process, as well as determining the geometric dimensions of the bone portion being restored. The porous mass plays the part of a matrix, on which the living bone tissue is formed. Provision of a layer of the porous mass between the rod and the shell allows efficient fixing of the tubular element on the rod.

Provision of a biomass of homogenized bone tissues in the porous mass promotes the regeneration process, which leads to a complete restoration of the missing portion of bone.

In a preferred embodiment of the present invention the shell is shaped as a telescopic structure made up of at least two tubular elements. This makes it possible to readily change the shell length during surgery in strict accordance with the length of the missing portion of bone, which makes possible the regeneration process and cuts down the operating time.

According to one of the embodiments of the present invention, the layer of porous polymer material is shaped as a bundle of fibers of biocompatible polymers.

Such an embodiment of the invention avoids the presence of free space between the rod and the shell, which adds to the reliability of holding the tubular element to the rod and improves the bone tissues regeneration conditions.

According to another embodiment of the invention the layer of porous polymer material is made of expanded hydrogel.

Such an embodiment likewise makes it possible to fill the entire space between the shell and the rod, facilitating biomass introduction and contributing to its uniform distribution and retention in the area of the missing portion of bone.

BRIEF DESCRIPTION OF THE DRAWINGS

Further objects and advantages of the present invention will become evident from the following detailed description of some specific exemplary embodiments thereof, with reference to the accompanying drawings, wherein.

DETAILED DESCRIPTION OF THE PREFERRED EMBODIMENTS

Figure 1:
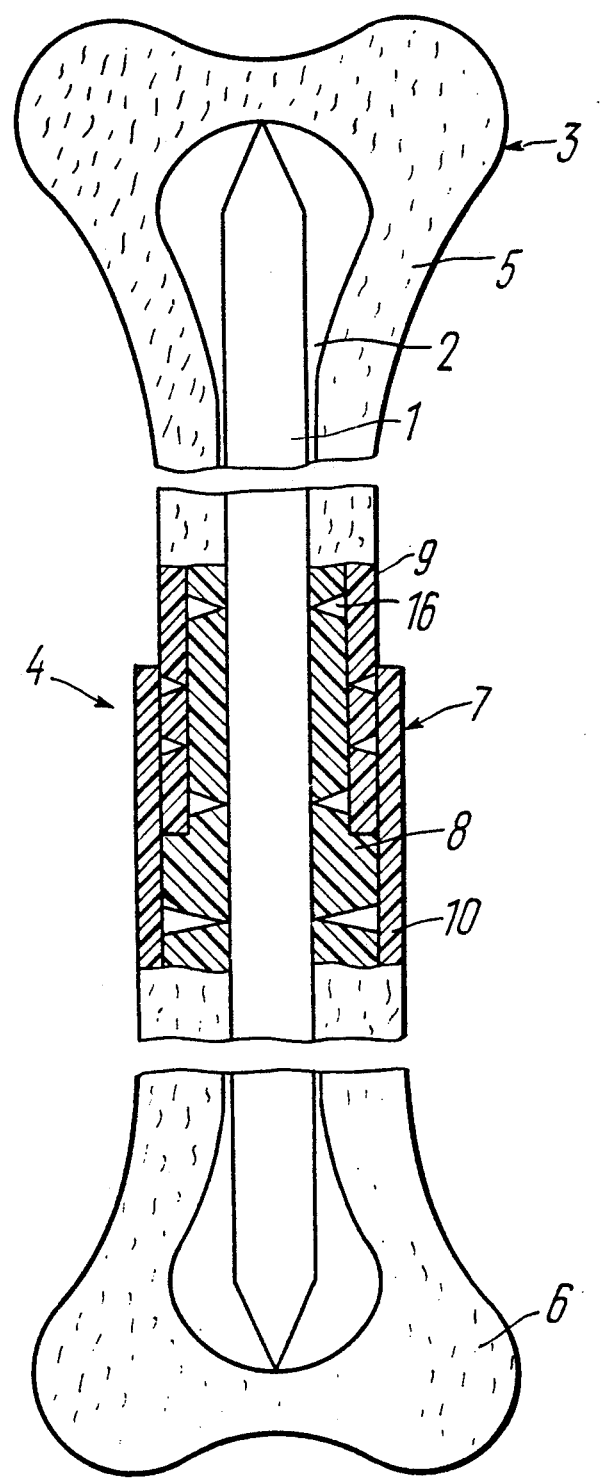
FIG. 1 is a schematic cross-sectional view of a device, according to the invention, installed in a tubular bone of a limb.

A device of the present invention includes a central rod 1 (FIG. 1) adapted to be introduced into a medullary canal 2 of an injured bone 3, and a tubular element 4 to be fitted on the rod 1 at the place of a missing portion of bone 3 so as to contact both of the bone fragments 5, 6 of the bone 3. The dimensions of the tubular element 4 correspond to the missing portion of bone 3 and tubular element 4 is shaped as a shell 7 of polymers biocompatible with the bone tissue. A layer 8 of a porous polymer material may be introduced between the rod 1 and the shell 7 for incorporating a biomass of homogenized bone tissues.

Figure 2:
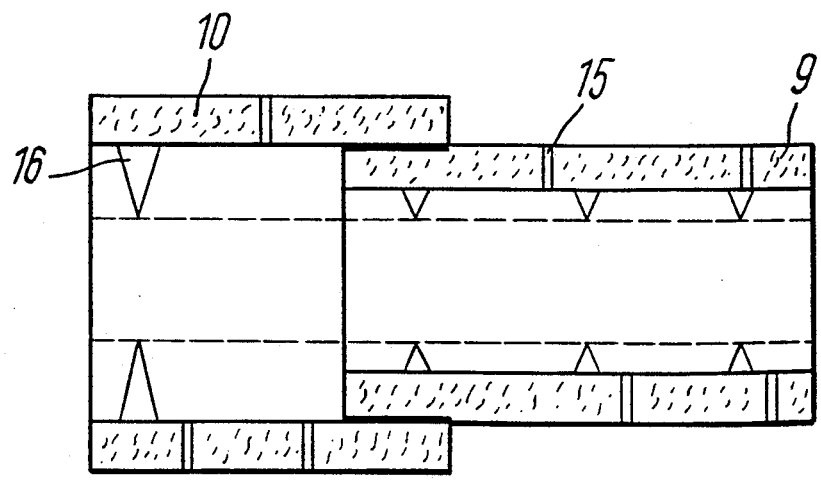
FIG. 2 is a schematic cross-sectional view of an embodiment of the shell construction.
Figure 3:
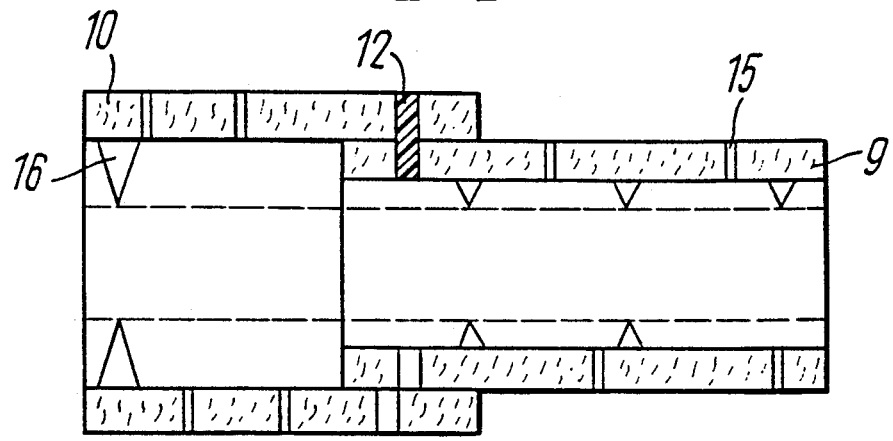
FIG. 3 is another schematic cross-sectional view of an embodiment of the shell construction.
Figure 4:
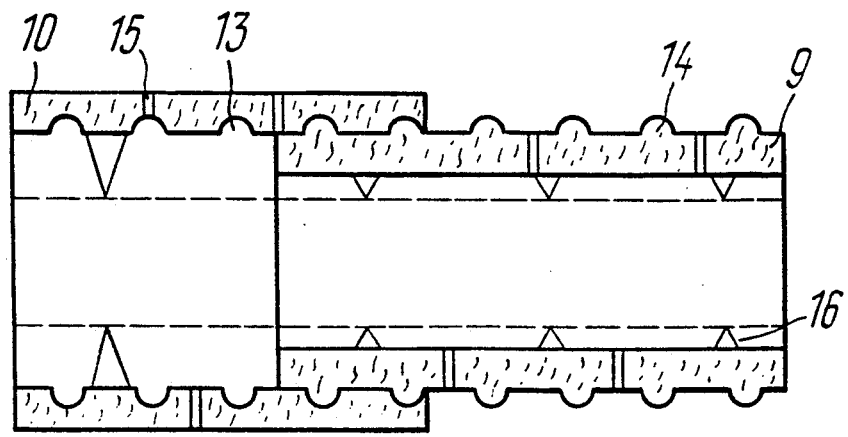
FIG. 4 is a further schematic cross-sectional view of an embodiment of the shell construction.

The shell 7 is shaped as a telescopic structure made up of at least two tubular elements 9, 10 (FIGS. 2 through 4), which are held together. The length of the shell 7 should be equal to the length of the missing portion of bone 3. The tubular elements 9, 10 of the shell 7 may be interlinked with the aid of a bonded joint 11 (FIG. 2), or a stud 12 (FIG. 3), as well as by a joint consisting of a recess 13 and a ridge 14 (FIG. 4).

The shell 7 is provided with radial holes 15, and fixing-and-supporting elements 16 (FIGS. 1 through 4) are provided on the inner surface of the tubular elements 9, 10.

The layer 8 of porous polymer material may be shaped as a bundle of fibers from biocompatible polymers or may be made of expanded hydrogel.

The device is fitted onto a patient as follows.

Prior to installing the device a set of components of the device having a standard size depending on the diameter of the central rod 1, which in turn correspond to the diameter of the medullary canal 2 of the injured bone 3, are selected. Upon withdrawing the rod 1, its length is adjusted by cutting so that after having been introduced into the proximal portions of the bone fragments 5, 6 the rod 1 is sized to ensure the same limb length as before the injury. The coaxial shell 7 is fitted onto the rod 1 approximately in its midportion with the aid of the supporting element 16, and the porous mass 8 is introduced between the rod 1 and the coaxial shell 7 as a bundle of fibers. When the porous mass is expanded hydrogel, it is introduced at a later stage along with the biomass. Then the rod 1 is introduced into the medullary canals 2 of both bone fragments 5 and 6 and the position assumed by the shell 7 is corrected so that the shell falls within the area of the missing portion of bone 3. Next, the length of the original limb is restored by completing the intramedullary introduction of the central rod 1 into the fragments 5, 6 of the bone 3 and the telescopic shell 7 is extended until the length is equal to the length of the missing portion of bone 3. As a result, the edges of shell 7 contact the ends of the fragments 5, 6 of the bone 3 and the length is fixed with the aid of one of the joints described above (FIGS. 2 through 4). Thereupon the mass is dispersed and introduced through one of the holes 15 into the porous mass appearing as a bundle of fibers.

When expanded hydrogel 8 is used as the porous mass, the biomass is first introduced into the hydrogel and then both the biomass and the hydrogel are introduced jointly through one of the holes 15 in the coaxial shell 7, into the space between the shell 7, the central rod 1 and the bone fragments 5, 6. The mixture is introduced until the biomass or its mixture with the expanded hydrogel 8 appears at the edges of both fragments 5, 6 of the bone 3. Then the wound is stitched up in layers and additional external immobilization is provided, when necessary.

Medicoexperimental studies of the device were carried out on experimental dogs. An annular bone fragment 30 to 35 mm long was removed from the femoral bone 3 under general anesthesia. A central rod 1 having a diameter of 8 mm, was introduced into the medullary canals 2 of both bone fragments 5 and 6 and the telescopic shell 7 was held to the rod 1. The inside diameter of the shell 7 was in excess of the diameter of the rod 1 by 5 or 6 mm.

The rod 1 was made of a copolymer of N-vinylpyrrolidone with methylmethacrylate reinforced with a mixture of capron fibers and aromatic polyamide fibers. A bundle of capron fibers and expanded hydrogel, incorporating an additive of the bone marrow and spongy bone of the same dog, were introduced into the space confined between the shell 7 and the rod 1. Just after surgery a large diastasis was observed between the bone fragments 5 and 6, corresponding to the length of the removed portion of the bone 3. In 141 days after surgery complete regeneration occurred and the medullary canal 2 was clearly discernible. The axis of the bone 3 was correct. The diameter of the restored bone portion was practically equal to the diameter of the original bone 3, only a hardly perceptible thickening of the bone 3 occurring on one side. Such positive results of experiments on test animals made it possible to recommend conducting clinical trials. Given below are specific examples of practical realization of the proposed technical solution.

EXAMPLE 1

Male patient V., 42. An area of the comminuted bone 3 38 mm long, resulting from an injury to the shin bone, had a medullary canal 2 of 11 mm in diameter. For the bone restoration procedure, use was made of a set, wherein the central rod 1 was a pin of a copolymer of N-vinylpyrrolidone with methylmethacrylate (the vinylpyrrolidone content being 28 to 32 molar percent) reinforced with capron fiber and incorporating an antimicrobial agent Dioxidine. The pin was shortened to be equal in length with the medullary canal 2 of the original bone 3 and was introduced retrogradely into one of the fragments 5 of the bone 3, whereupon the coaxial telescopic shell 7 was held to the pin, the shell being made of a copolymer of N-vinylpyrrolidone with butylmethacrylate (the vinylpyrrolidone content being 48 to 56 molar percent), the copolymer containing 25 percent of a mixture of Dioxidine and Quinoxidine (1:2) and reinforced with four layers of capron fiber containing Gentamycin. The inside diameter of the shell was 16 mm, while the two portions thereof were each 45 mm long. The shells 7 were provided with three supporting elements 16 to be held to the rod 1. One of the shells 7 (the inner shell) was provided with four pairs of recesses 13, whereas the other (outer) shell 7 had four pairs of fixing ridges 14. Insertion of the third pair of ridges 14 into the third pair of recesses 13 brought the total length of the shell 7 to about 38 mm. Then a bundle of acid-treated capron fiber was introduced into the shell 7. After the rod 1 had been introduced into the bone fragment 6 and the shell 7 had been installed at the place of the bone missing fragment, pulp consisting of residuals of the patient's bone marrow and the spongy component of the fragments of the lost bone 3 was introduced into the bundle of fibers through one of the holes 15 until pulp appeared at the edges of the bone fragments 5, 6. Finally, the wound was stitched up in layers and a coaxial dressing was applied. Complete restoration of the fragment of the missing portion ensued in 86 days.

EXAMPLE 2

Male patient K. Missing portion of the femoral bone, 43 mm long. A central rod 1 of 14 mm diameter, made of a pin of a copolymer of N-vinylpyrrolidone and methylmethacrylate reinforced with modified capron fiber and a coaxial shell 7 having a total length of its two portions 9, 10 equal to 45 mm, were used. The shell was made of a mixture of copolymers (in the ratio of 1:3) of vinylpyrrolidone with methylmethacrylate and of vinylpyrrolidone with butylmethacrylate, containing 5 percent of Gentamycin and 5 percent of orotic acid, reinforced with capron fiber. The porous mass was introduced between the rod 1 and the shell 7, the mass being based on expanded hydrogel from a copolymer of N-vinylpyrrolidone, acrylamide and ethylacrylate, including a biomass, i.e., homogenate of the bone marrow. After stitching up the wound, an external immobilization apparatus was applied. Complete restoration of the lost fragment of the bone 3 ensued in 94 days.

EXAMPLE 3

Male patient L. Missing portion of the humeral bone, 27 mm long. Use was made, as in Example 1, of a rod 1 made of the same material and having a diameter of 9 mm, of the coaxial shell 7 having two portions, 9 and 10, each 25 mm long and made of a mixture of polyethylcyanacrylate and a copolymer of vinylpyrrolidone with butylmethacrylate, containing 20 percent of a mixture of Gentamycin, orotic acid, and sea-buckthorn oil (5:4:1) and reinforced with two layers of acid-treated capron fiber. The porous mass incorporated a mixture of carboxymethyl cellulose fibers and capron fibers coated with a copolymer of vinylpyrrolidone with butylmethacrylate, containing Gentamycin, sea-buckthorn oil, and homogenate of the patient's bone marrow. Complete restoration of the lost portion of bone 3 ensued in 82 days.

EXAMPLE 4

Male patient Sh. Missing portion of the femoral bone 3, 48 mm long. Use was made, as in Example 1, of a rod 1 made of the same material and having a diameter of 12 mm, and of a coaxial shell 7 having two portions 15, 16 having four fixing elements each and made of a mixture of copolymers of vinylpyrrolidone with methylmethacrylate and of vinylpyrrolidone with butylmethacrylate, the shell comprising a mixture of with butylmethacrylate, the shell comprising a mixture of Dioxidine and Quinoxidine and being reinforced with four layers of capron fiber, containing Gentamycin. The porous mass was in the form of a bundle made up of capron fiber coated with a copolymer and incorporating sea-buckthorn oil and Gentamycin, and the biomass was in the form of a pulp of the spongy bone in donor's blood. After stitching up the wound, a plaster-of-Paris dressing was applied. Complete restoration of the lost portion of bone took 102 days.

To proposed device makes it possible to completely restore missing fragments of tubular bones, involving formation of a patient's own bone of the original dimensions.

A total treatment course with the use of a prior art device ranges between 300 and 360 days, whereas that with the use of the proposed device lasts from 90 to 100 days. No complications after application of the proposed device occurred.

The invention finds utility when applied to restoration of missing portions of bone due to total defects of long tubular bones following extensive injuries or wounds, or after large pathological changes of the bone tissue (e.g., tumors or tuberculous infections).

What is claimed is:

1. A device for restoration of a missing portion of a tubular bone, comprising a central rod (1) insertable into a medullary canal (2) of distal and proximal fragments (5, 6) of a bone (3) and a tubular element (4) disposed coaxially on the rod (1) in place of the missing portion of the bone and being radially substantially equidimensional at each end with the missing portion of the bone (3), wherein the tubular element (4) comprises a shell (7) of adjustable length made from polymers biocompatible with the bone tissue, and a layer (8) of porous polymer material incorporating homogenized bone tissue is disposed between the rod (1) and the shell (7).

2. A device as claimed in claim 1, wherein the shell (7) is a telescopic structure comprising at least two tubular elements (9, 10).

3. A device as claimed in claim 1, wherein the layer (8) of comprises porous polymer material bundles comprises bundles of fibers.

4. A device as claimed in calim 1, wherein the layer (8) of a porous polymer material comprises formed hydrogel.

* * * * *